(12) United States Patent
Okiyama et al.

(10) Patent No.: US 9,283,366 B2
(45) Date of Patent: Mar. 15, 2016

(54) MEDICAL PORT

(75) Inventors: Tadashi Okiyama, Hiroshima (JP); Hitoshi Tachizaki, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 321 days.

(21) Appl. No.: 13/061,673

(22) PCT Filed: Aug. 28, 2009

(86) PCT No.: PCT/JP2009/065110
§ 371 (c)(1),
(2), (4) Date: Mar. 1, 2011

(87) PCT Pub. No.: WO2010/024407
PCT Pub. Date: Mar. 4, 2010

(65) Prior Publication Data
US 2011/0160679 A1   Jun. 30, 2011

(30) Foreign Application Priority Data

Sep. 1, 2008  (JP) ................................. 2008-223859
Aug. 26, 2009  (JP) ................................. 2009-195875

(51) Int. Cl.
*A61M 39/04*  (2006.01)
*A61M 39/02*  (2006.01)
(Continued)

(52) U.S. Cl.
CPC ............. *A61M 39/045* (2013.01); *A61M 39/02* (2013.01); *A61M 39/04* (2013.01); *A61M 39/26* (2013.01); *A61M 2039/0036* (2013.01); *A61M 2039/0072* (2013.01)

(58) Field of Classification Search
CPC ..... A61M 5/00; A61M 39/045; A61M 39/02; A61M 39/04; A61J 2001/2051; A61J 1/10; A61J 1/1475; A61J 1/1406
USPC ................ 604/167.01–167.05, 256, 259, 249
See application file for complete search history.

(56) References Cited

U.S. PATENT DOCUMENTS 5,300,034 A * 4/1994 Behnke et al. ............ 604/167.02
5,407,433 A * 4/1995 Loomas .................... 604/167.06
5,458,640 A * 10/1995 Gerrone ........................ 604/264
(Continued)

FOREIGN PATENT DOCUMENTS

JP      6-039011     5/1994
JP      11-197254    7/1999
(Continued)

*Primary Examiner* — Aarti B Berdichevsky
*Assistant Examiner* — Matthew A Engel
(74) *Attorney, Agent, or Firm* — Hamre, Schumann, Mueller & Larson, P.C.

(57) ABSTRACT

A medical port includes a disc-shaped valve 1 in which an insertion hole is formed in a central portion 1a, a base seat 7 that supports the valve from a lower surface side, and a cover 2 that has a fitting hole exposing an upper surface of the central portion of the valve and covers at least a peripheral edge of the valve from the upper surface side, the fitting hole being formed so that when an inserting body has been inserted into the insertion hole, a fit between the inserting body and the fitting hole can cause the inserting body to be locked against the cover. An annular protrusion 1d is formed in the valve 1, the annular protrusion being continuous in the circumferential direction, and formed in the valve 1 so that in the state in which the inserting body is locked against the cover, the annular protrusion is in contact with an outer circumferential surface of a leading end portion of the inserting body.

10 Claims, 21 Drawing Sheets

(51) Int. Cl.
*A61M 39/26* (2006.01)
*A61M 39/00* (2006.01)

(56) References Cited

U.S. PATENT DOCUMENTS

| | | | | |
|---|---|---|---|---|
| 5,584,808 | A * | 12/1996 | Healy | 604/86 |
| 5,827,228 | A * | 10/1998 | Rowe | 604/167.02 |
| 5,957,898 | A * | 9/1999 | Jepson | A61M 39/045 128/912 |
| 6,468,251 | B1 * | 10/2002 | Yamanaka et al. | 604/256 |
| 6,695,817 | B1 * | 2/2004 | Fangrow, Jr. | A61M 39/02 251/149.1 |
| 6,699,215 | B2 * | 3/2004 | Fujii | 604/82 |
| 6,699,221 | B2 * | 3/2004 | Vaillancourt | A61M 25/0606 604/164.13 |
| 6,908,459 | B2 * | 6/2005 | Harding | A61M 39/045 604/256 |
| 6,916,309 | B2 * | 7/2005 | Fangrow, Jr. | A61M 39/02 251/149.1 |
| 7,025,744 | B2 * | 4/2006 | Utterberg | A61M 39/02 604/256 |
| 7,303,542 | B2 * | 12/2007 | Fujii | 604/82 |
| 7,568,509 | B2 * | 8/2009 | Py | 141/301 |
| 7,753,338 | B2 * | 7/2010 | Desecki | A61M 39/045 251/149.6 |
| 8,066,669 | B2 * | 11/2011 | Christensen | A61M 5/36 604/122 |
| 8,066,670 | B2 * | 11/2011 | Cluff | A61M 25/00 604/122 |
| 8,337,483 | B2 * | 12/2012 | Harding | A61M 39/045 604/122 |
| 8,475,416 | B2 * | 7/2013 | Lynn | A61M 39/02 604/256 |
| 8,512,294 | B2 * | 8/2013 | Ou-Yang | A61M 39/045 604/167.03 |
| 8,540,677 | B2 * | 9/2013 | McKinnon | A61M 39/045 604/167.04 |
| 8,585,661 | B2 * | 11/2013 | Okiyama | A61M 39/045 604/249 |
| 2005/0192537 | A1 * | 9/2005 | Osborne et al. | 604/167.01 |
| 2006/0184140 | A1 * | 8/2006 | Okiyama | 604/249 |

FOREIGN PATENT DOCUMENTS

| | | |
|---|---|---|
| JP | 11-276595 | 10/1999 |
| JP | 2008-529672 | 8/2008 |
| WO | 2004/032707 | 4/2004 |
| WO | 2005/004973 | 1/2005 |
| WO | 2008/045761 | 4/2008 |

\* cited by examiner

MEDICAL PORT

TECHNICAL FIELD

The present invention relates to a medical port through which a liquid such as a drug solution can be injected and/or collected.

BACKGROUND ART

When a drug solution or the like is administered to a patient, a drug solution that is different from the principal drug solution may be coinjected into a liquid feed passage for drug solution supply, or a liquid flowing through the above-described liquid feed passage may be sampled. In such cases, conventionally, a plug made of rubber is provided in the liquid feed passage as a coinjection port, and the plug is pierced with an injection needle or the like to coinject the drug solution or to collect the liquid.

However, there has been a problem in that if a region of the plug other than a predetermined region to be pierced is pierced with the needle, liquid leakage from that position may occur. In addition, there has been a problem of contamination of the needle due to, for example, a mistake in operation. Recently, a medical port whereby an inserting body whose tip is not sharp can be inserted and held in an insertion hole formed in a valve has been proposed. Patent Document 1 discloses, as an example of a medical port such as this, a medical port having a valve that is adapted so that when, for example, a luer (an inserting body) constituting a syringe tip is pushed into an insertion hole, a liquid can be injected and/or collected, and when the luer is withdrawn from the insertion hole, the insertion hole closes due to its elasticity (see Patent Document 1, for example).

CITATION LIST

Patent Document

Patent document 1: JP 11-197254A

DISCLOSURE OF INVENTION

Problem to be Solved by the Invention

However, there have been cases where insertion of the above-described inserting body into the insertion hole in a manner that applies an excessive load to the valve by, for example, thrusting the inserting body into the insertion hole while turning the inserting body around its axis results in leakage of the liquid from the insertion hole.

Thus, the present invention provides a medical port that further suppresses the occurrence of liquid leakage.

Means for Solving Problem

A medical port of the present invention includes:
a disc-shaped valve in which an insertion hole is formed in a central portion;
a base seat that supports the valve from a lower surface side; and
a cover that has a fitting hole exposing an upper surface of the central portion of the valve and covers at least a peripheral edge of the valve from the upper surface side,
the fitting hole being formed so that when an inserting body has been inserted into the insertion hole, a fit between the inserting body and the fitting hole can cause the inserting body to be locked against the cover,
wherein an annular protrusion is formed in the valve,
the annular protrusion being formed in the valve so that in the state in which the inserting body is locked against the cover, the annular protrusion is in contact with an outer circumferential surface of a leading end portion of the inserting body.

Effects of the Invention

In the medical port of the present invention, the annular protrusion is formed in the valve so that in the state in which the inserting body is locked against the cover, the annular protrusion is in contact with the outer circumferential surface of the leading end portion of the inserting body. Thus, the tightness of contact between the outer circumferential surface of the leading end portion of the inserting body and the valve is improved, and so the occurrence of liquid leakage is suppressed.

DESCRIPTION OF THE INVENTION

As described above, there have been cases where insertion of an inserting body into the insertion hole in a manner that applies an excessive load to the valve by, for example, thrusting the inserting body into the insertion hole results in liquid leakage from the insertion hole. The inventors of the present invention have investigated the cause of the liquid leakage and found that the leakage is caused by a reduction in the sealing properties provided by the valve, as described below.

When an inserting body has been inserted into the insertion hole in a manner that applies an excessive load to the valve by, for example, thrusting the inserting body into the insertion hole, a crack may occur in particular in an inner surface of the valve defining both ends of the insertion hole in the longitudinal direction and their vicinity. In the case where the insertion hole is a slit, a crack may occur at both ends of the slit in the longitudinal direction and in their vicinity. It is conceivable that a crack occurring in the inner surface of the valve leads to a reduction in an elastic force (restoring force) of a portion of the valve that comes in contact with an outer circumferential surface of a leading end portion of the inserting body, and this reduction in the restoring force reduces the tightness of contact between the valve and the outer circumferential surface of the leading end portion the inserting body and hence may cause the above-described liquid leakage.

Next, the cause of liquid leakage will be described in greater detail using an example of a conventional medical port with which the above-described liquid leakage is considered to be likely to occur. However, the valve constituting the present invention is not limited to a form having a notch that will be described later. Even in the case of a valve that has no notch, for example, a valve that has an approximately uniform thickness (e.g., a valve whose upper surface and lower surface are both flat), a crack may occur in the inner surface of the valve, and for this reason, the valve constituting the present invention also may be a valve having an approximately uniform thickness.

Figure 24A:
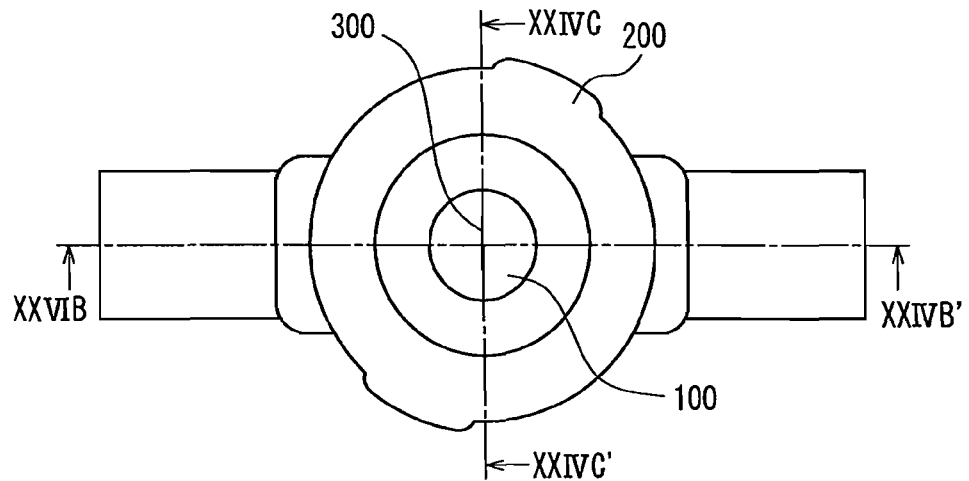
FIG. 24A is a plan view of an example of a conventional medical port.
Figure 24B:
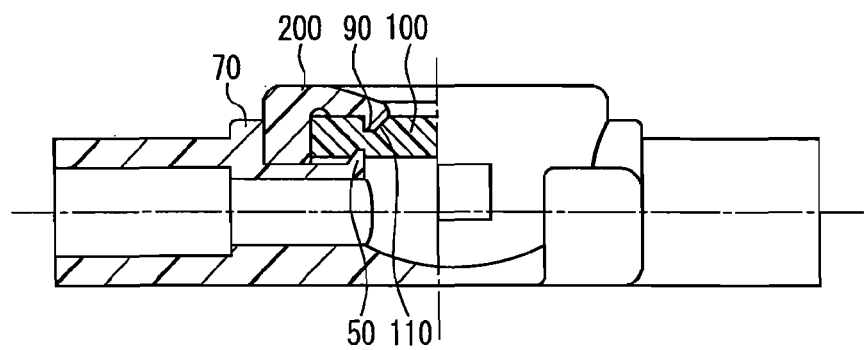
FIG. 24B is a cross-sectional view taken along line XXIVB-XXIVB' in FIG. 24A.
Figure 24C:
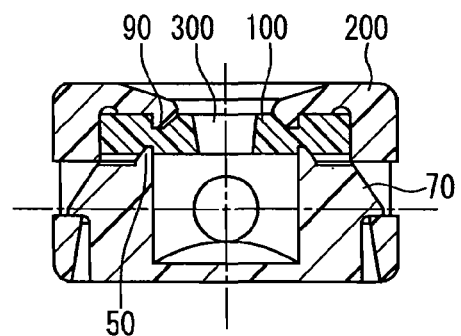
FIG. 24C is a cross-sectional view taken along line XXIVC-XXIVC' in FIG. 24A.
Figure 25:
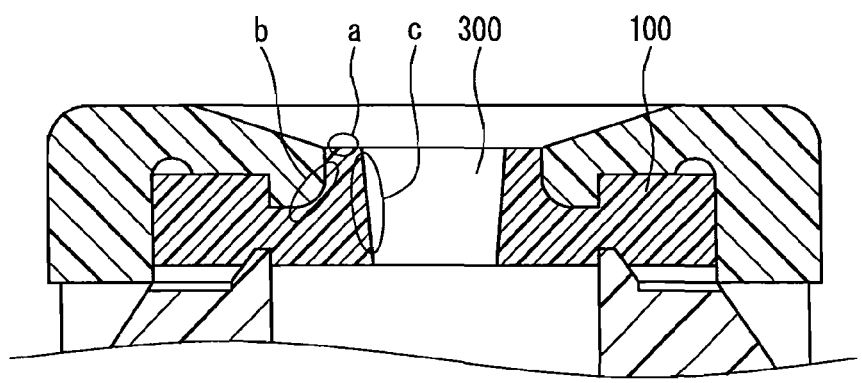
FIG. 25 is a partial enlarged view of the conventional medical port shown in FIG. 24C.
Figure 26:
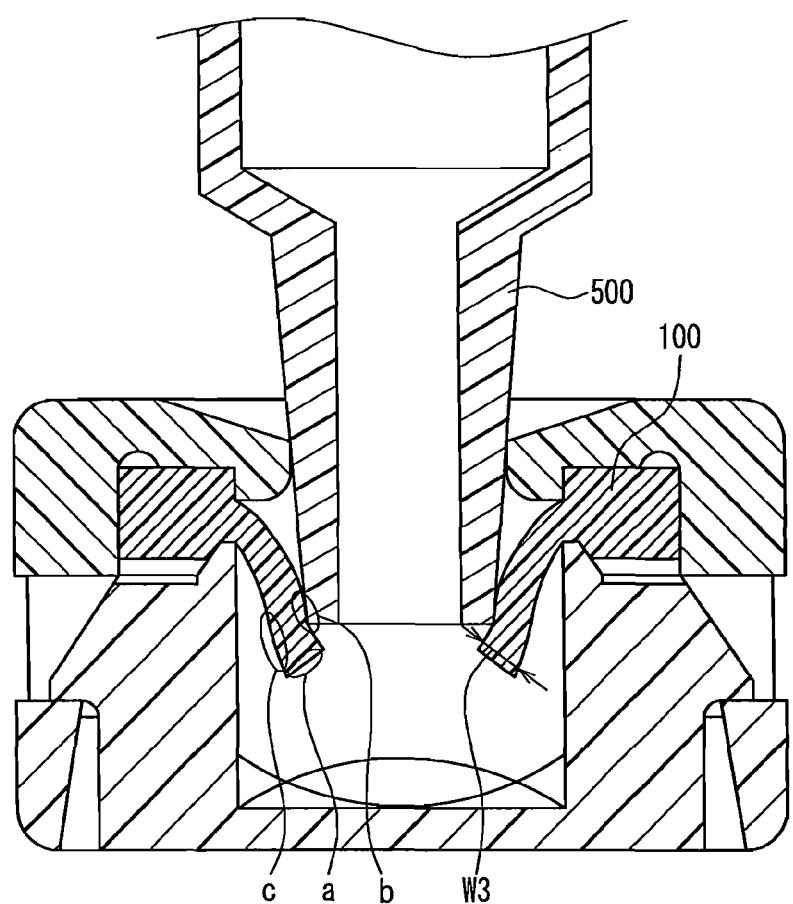
FIG. 26 is a cross-sectional view showing a state at the time when an inserting body has been inserted into an insertion hole of the medical port shown in FIG. 24C.

FIG. 24A is a plan view of an example of a conventional medical port, FIG. 24B is a cross-sectional view taken along line XXIVB-XXIVB' in FIG. 24A, FIG. 24C is a cross-sectional view taken along line XXIVC-XXIVC' in FIG. 24A, FIG. 25 is a partial enlarged view (a cutting plane as seen when the conventional medical port is cut in a direction that is parallel to the longitudinal direction of an insertion hole 300) of the conventional medical port shown in FIG. 24C, and FIG. 26 is a cross-sectional view showing a state at the time when an inserting body has been inserted into the insertion hole of the medical port shown in FIG. 24C.

In the conventional medical port, as shown in FIGS. 24A to 24C, a valve 100 has an annular notch 110 in a surface (upper surface) thereof. In this medical port, the valve 100 is held by a base seat 70 having an annular projection 50 and a cover 200 having a hook portion 90, and the notch 110 and the hook portion 90 of the cover 200 are in engagement with each other. Thus, the valve 100 is divided into an elongation portion inside the annular projection 50 and a compression portion outside the annular projection 50. That is to say, once an inserting body is inserted into the insertion hole 300 of the valve 100, the elongation portion elongates due to the insertion of the inserting body. On the other hand, since the compression portion is compressed by the cover 200 and the base seat 70, the compression portion does not elongate even when the inserting body is inserted into the insertion hole.

In the state in which an inserting body 500 has been inserted into the insertion hole as shown in FIG. 26, a portion b of the elongation portion of the valve 100 is in contact with an outer circumferential surface of a leading end portion of the inserting body 500 as is apparent from FIGS. 25 and 26. Thus, if the tightness of contact between the portion b and the outer circumferential surface of the leading end portion of the inserting body 500 decreases at any position in the circumferential direction in a region where the portion b in the upper surface of the valve is in tight contact with the outer circumferential surface of the leading end portion of the inserting body 500, the possibility that a liquid may leak from the insertion hole 300 increases.

When the inserting body 500 has been inserted into the insertion hole 300 in a manner that applies an excessive load to the valve 100 by, for example, thrusting the inserting body into the insertion hole 300, a crack may occur in particular in a portion c (an inner surface of the valve 100 that defines either end of the insertion hole 300 in the longitudinal direction and its vicinity) of the valve. A crack occurring in the portion c of the valve 100 leads to a reduction in the elastic force (restoring force) of a portion of the valve 100 that comes in contact with the outer circumferential surface of the leading end portion of the inserting body 500, and this reduction in the restoring force reduces the tightness of contact between the portion b and the outer circumferential surface of the leading end portion of the inserting body 500 and may hence cause the above-described liquid leakage. In particular, in the conventional medical port that is described using FIGS. 24A to 26, it is conceivable that the extent of a detrimental effect of a crack in the valve on the sealing properties is significant because the portion b is part of a portion of the valve 100 that has a relatively small thickness.

It should be noted that the size of the area of contact between the portion b and the outer circumferential surface of the leading end portion of the inserting body can be determined by X-ray CT or the like. Whether or not a crack has occurred in the above-described portion c can be determined based on a change in the thickness W3 of a portion a of the valve when the inserting body 500 is in an inserted state in which it has been inserted into the insertion hole 300. The change in the thickness W3 can be determined by X-ray CT or the like as well. The thickness W3 in the case where a crack has occurred in the portion c is smaller than the thickness W3 in the case where no crack has occurred.

Thus, the inventors of the present invention formed an annular protrusion in the valve, the annular protrusion coming in contact with the outer circumferential surface of the leading end portion of the inserting body in the state in which the inserting body is locked against the cover, so as to sufficiently secure the area of contact between the valve and the outer circumferential surface of the leading end portion of the inserting body and thus increase the tightness of contact between them.

Embodiment 1

Next, an example of a medical port according to Embodiment 1 of the present invention will be described using FIGS. 1 to 12.

Figure 1:
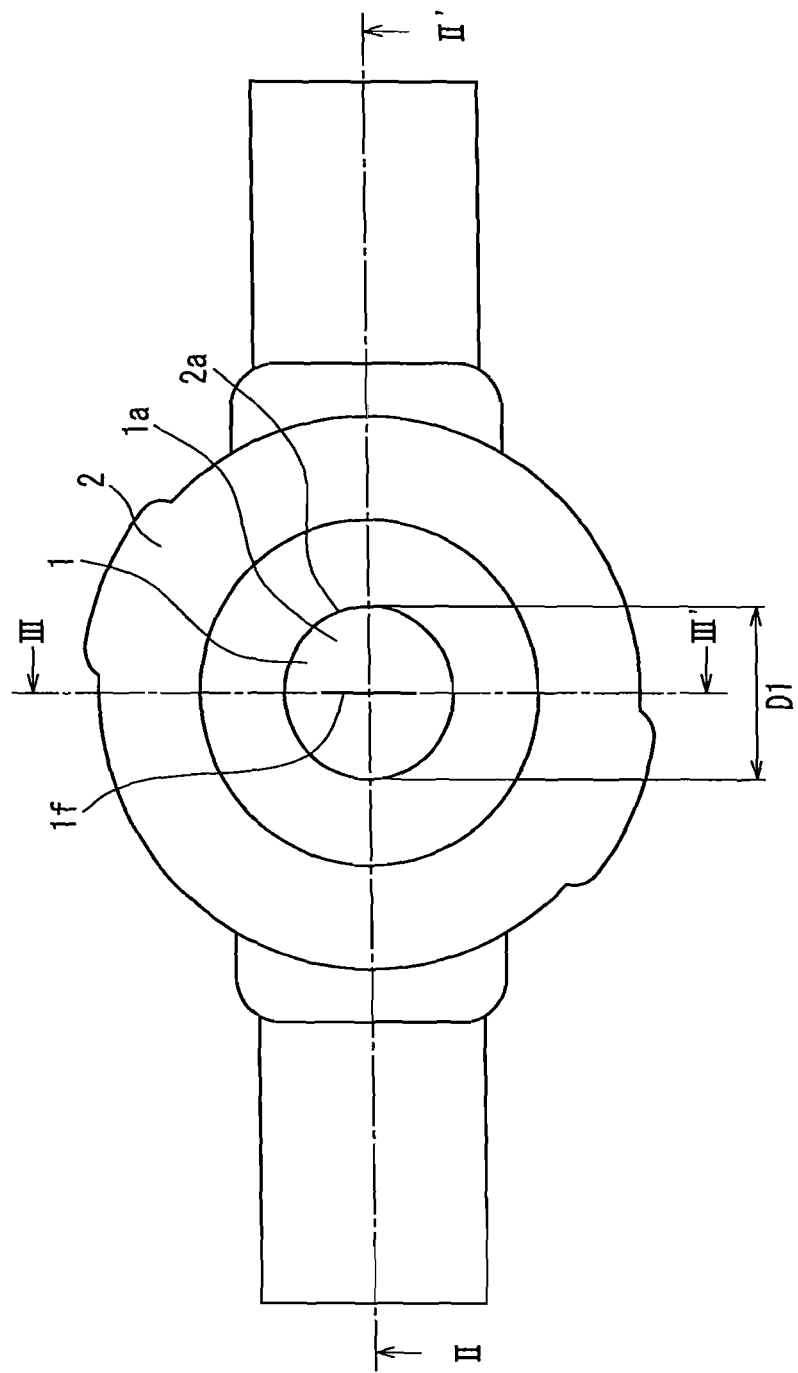
FIG. 1 is a plan view for explaining an example of a medical port according to Embodiment 1 of the present invention.
Figure 2:
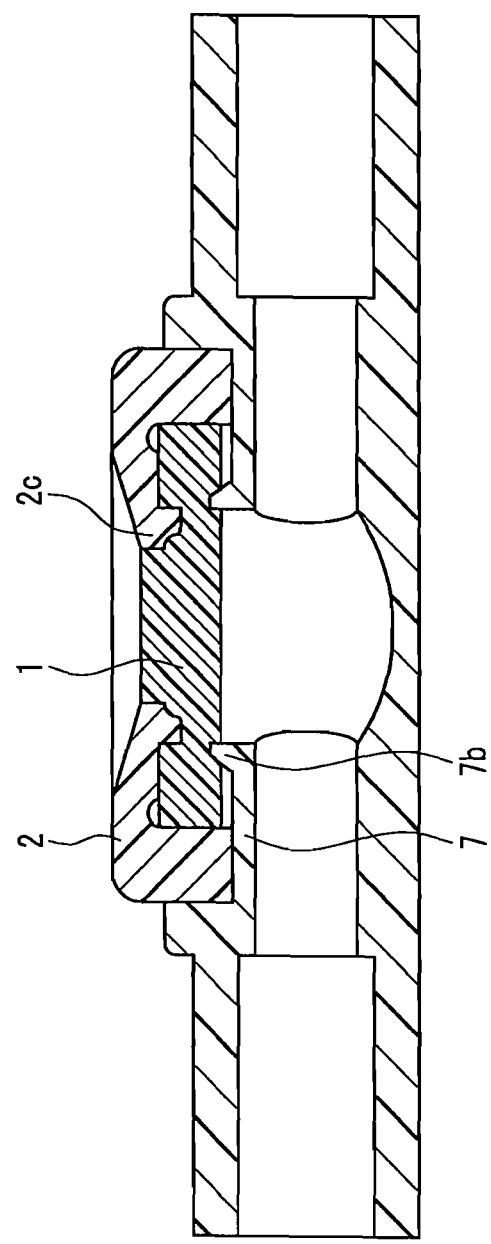
FIG. 2 is a cross-sectional view of the medical port shown in FIG. 1 taken along line II-II'.
Figure 3:
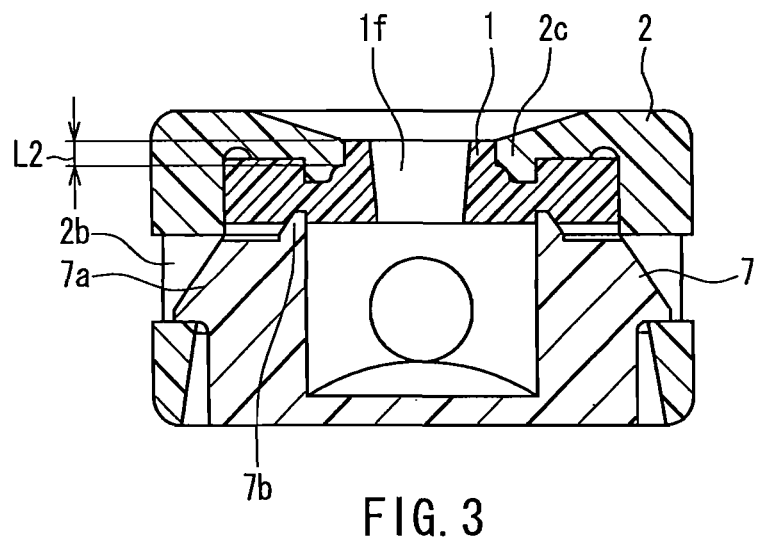
FIG. 3 is a cross-sectional view of the medical port shown in FIG. 1 taken along line III-III'.

As shown in FIGS. 1 to 3, the example of the medical port of the present invention includes a disc-shaped valve 1, a base seat 7 that supports a peripheral edge of the valve from a lower surface side of the valve, and a cover 2.

Figure 4:
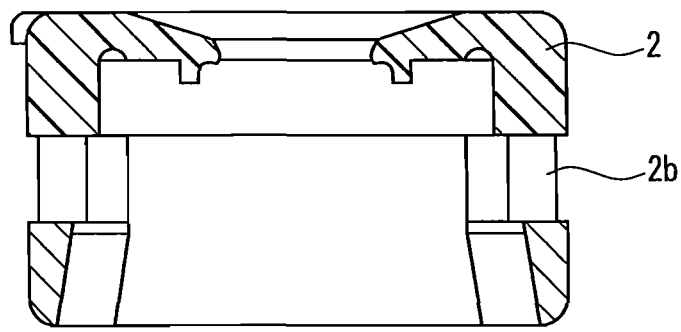
FIG. 4 is a cross-sectional view of a cover constituting the medical port shown in FIG. 1.

As shown in FIG. 1, the cover 2 has, for example, an approximately circular shape when viewed from above. The cover 2 has a fitting hole 2a through which an upper surface of a central portion 1a of the valve 1 can be exposed. As shown in FIG. 4, the cover 2 has, for example, at least two notches 2b in lateral portions thereof the notches 2b are engaged with projections 7a (see FIG. 3) of the base seat 7, and thus the valve 1 is held by the base seat 7 and the cover 2. Assuming that a luer at the tip of a common syringe or a luer of a male connector constituting an infusion or a transfusion set is used as the inserting body, preferably, the diameter D1 of the fitting hole 2a is set to a value within a range of 3.9 to 4.4 mm and the thickness L2 (see FIG. 3) of the fitting hole 2a is set to a value within a range of 0.3 to 1.0 mm; and more preferably, the diameter D1 is set within a range of 3.9 to 4.2 mm and the thickness L2 is set within a range of 0.4 to 0.7 mm. With this configuration, it is possible to lock the inserting body against the cover 2 with a simple structure and in a reliable manner.

Preferably, the cover 2 has a sufficient strength so as not to break even when the inserting body is fitted securely into the fitting hole 2a. For example, polyacetal, polypropylene, polyamide, polyethylene terephthalate, and polybutylene terephthalate are preferable as the material for the cover 2 in view of the chemical resistance, heat resistance, and the like.

The cover 2 preferably has an annular hook portion 2c (see FIGS. 2 and 3, for example) engageable with an annular groove 1c (see FIGS. 6 to 8, for example) of the valve 1. Moreover, the base seat 7 preferably has an annular projection 7b that is formed along a peripheral edge portion of a hole provided in the base seat 7 and that is positioned outwardly from the annular hook portion 2c in the radial direction. In this medical port, since the valve 1 is held firmly by the base seat 7 having the annular projection 7b and the cover 2 having the annular hook portion 2c, and the annular groove 1c and the annular hook portion 2c of the cover 2 are in engagement with each other, the valve 1 is divided into an elongation portion inside the annular projection 7b and a compression portion outside the annular projection 7b. That is to say, once the inserting body is inserted into an insertion hole 1f of the valve 1, the elongation portion elongates due to the insertion of the inserting body. On the other hand, the compression portion is compressed by the cover 2 and the base seat 7 and therefore does not elongate even when the inserting body is inserted into the insertion hole. Thus, prevention of liquid leakage between the valve 1 and the base seat 7 and satisfactory restoration of the elongated valve 1 can be made mutually compatible.

Figure 5:
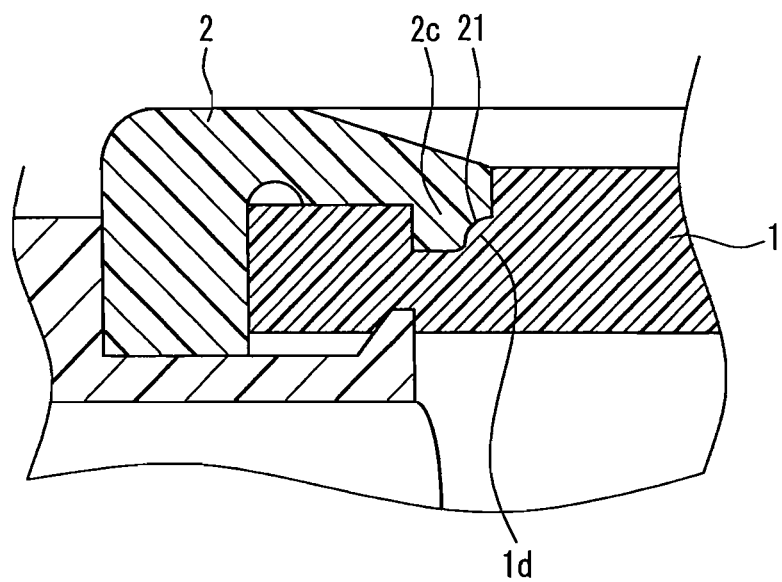
FIG. 5 is a partial enlarged view of the medical port shown in FIG. 2.

As shown in FIG. 5, preferably, an annular depression 21 corresponding to an annular protrusion 1d of the valve 1 is formed in a surface of the annular hook portion 2c of the cover 2 that is in contact with the valve 1. In this case, deformation of the annular protrusion 1d under the pressure exerted by the annular hook portion 2c can be suppressed, and consequently, a reduction in an effect of improving the tightness of contact of an inner surface of the insertion hole 1f with the outer circumferential surface of the leading end portion of the inserting body, which may be caused by the above-described deformation of the annular protrusion 1d, and a reduction in an effect of suppressing liquid leakage from the insertion hole 1f which is due to the reduction in the tightness of contact, can be suppressed. In other words, in the case where the annular depression 21 corresponding to the annular protrusion 1d of the valve 1 is formed in the surface of the annular hook portion 2c that is in contact with the valve 1, liquid leakage from the insertion hole 1f can be suppressed more effectively.

Figure 6:
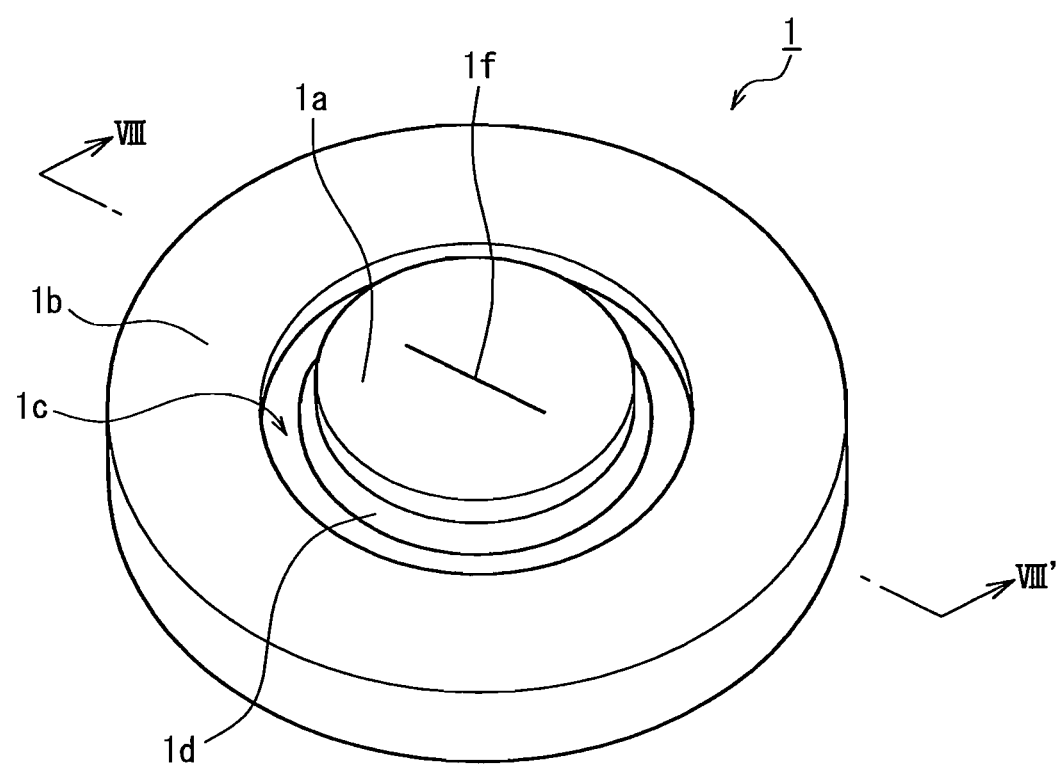
FIG. 6 is a perspective view of a valve constituting the medical port shown in FIG. 1.
Figure 7:
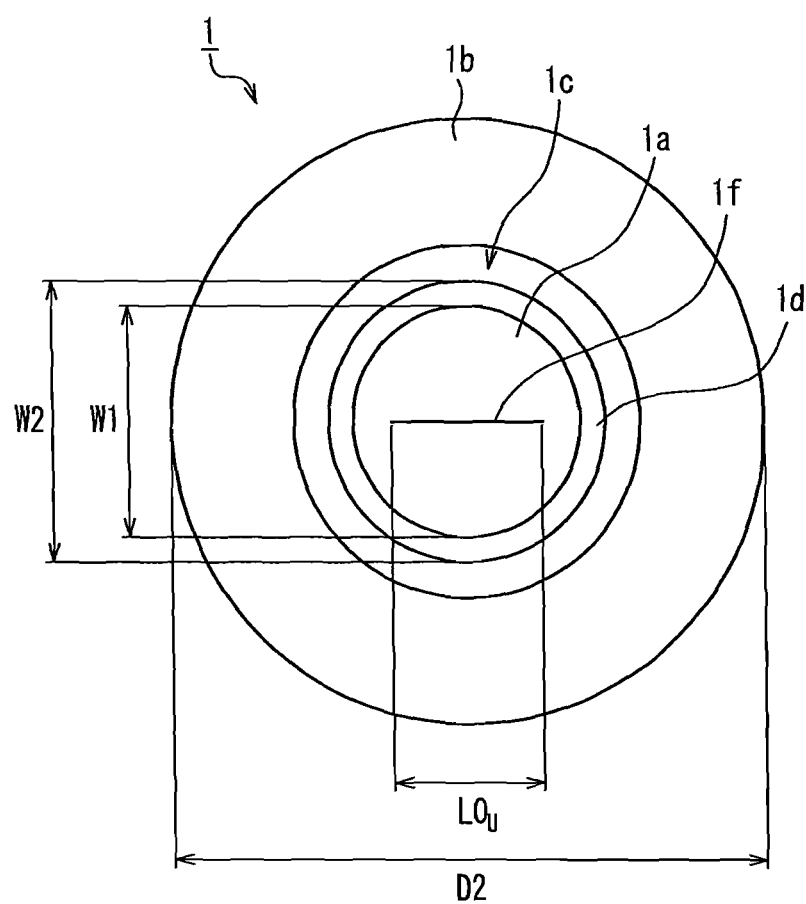
FIG. 7 is a plan view of the valve shown in FIG. 6.
Figure 8:
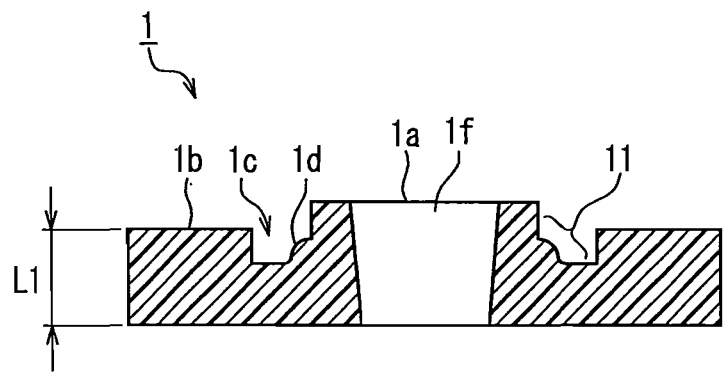
FIG. 8 is a cross-sectional view of the valve shown in FIG. 6 taken along line VIII-VIII'.

As shown in FIGS. 6 to 8, the annular groove 1c is formed in the upper surface of the valve 1. Thus, in the valve 1, the thickness of a portion around the central portion in which the insertion hole 1f is formed is smaller than that of the central portion. Moreover, the thickness of a portion (peripheral edge portion) 1b of the valve 1 outside the annular groove 1c is greater than the thickness of a portion of the valve 1 in which the annular groove 1c is formed. In this case, when the inserting body is inserted into the insertion hole 1f a relatively small thickness part of the elongation portion of the valve 1 stretches well. Accordingly, when compared to a valve whose elongation portion has a constant thickness, the ease of insertion of the inserting body is improved, and the state in which the inserting body is fitted in the fitting hole is well retained.

In the valve 1, the annular protrusion 1d is formed in a stepped surface 11 (see FIG. 8) formed by decreasing the thickness of the portion around the central portion 1a of the valve 1 to a smaller thickness than that of the central portion 1a. In the present invention, the stepped surface refers to a surface that defines part of the upper surface of the valve and that is a connecting surface connecting the upper surface of the central portion of the valve to the upper surface of a minimum thickness part of the portion around the central portion of the valve. The stepped surface may be a vertical surface that forms an angle of 90 degrees with the upper surface of the central portion of the valve or may be an inclined surface. The inclined surface may be linearly inclined or may be inclined in a curved manner. It is assumed that the annular protrusion is formed in the above-described stepped surface even if part of the annular protrusion 1d is formed in the stepped surface and the rest is formed in the upper surface of the valve in the minimum thickness part of the portion around the central portion.

There is no particular limitation to, in particular, the shape and the like of the annular protrusion 1d as long as the annular protrusion 1d comes in contact with the outer circumferential surface of the leading end portion of the inserting body when the inserting body is in a state in which it is locked against the cover 2, and acts so as to improve the tightness of contact between the outer circumferential surface of the leading end portion of the inserting body and the valve. However, the annular protrusion 1d is preferably formed at a position in the above-described stepped surface 11 that is below the upper surface of the central portion 1a of the valve 1, for the following reasons.

Figure 9:
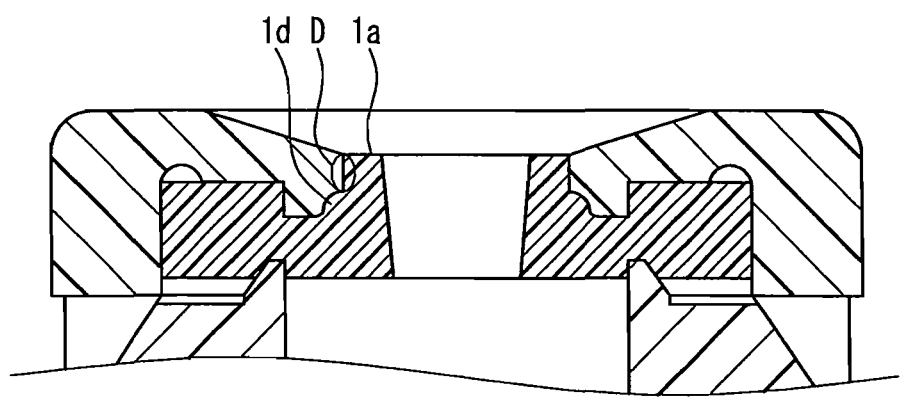
FIG. 9 is an enlarged view of the medical port shown in FIG. 3.
Figure 10:
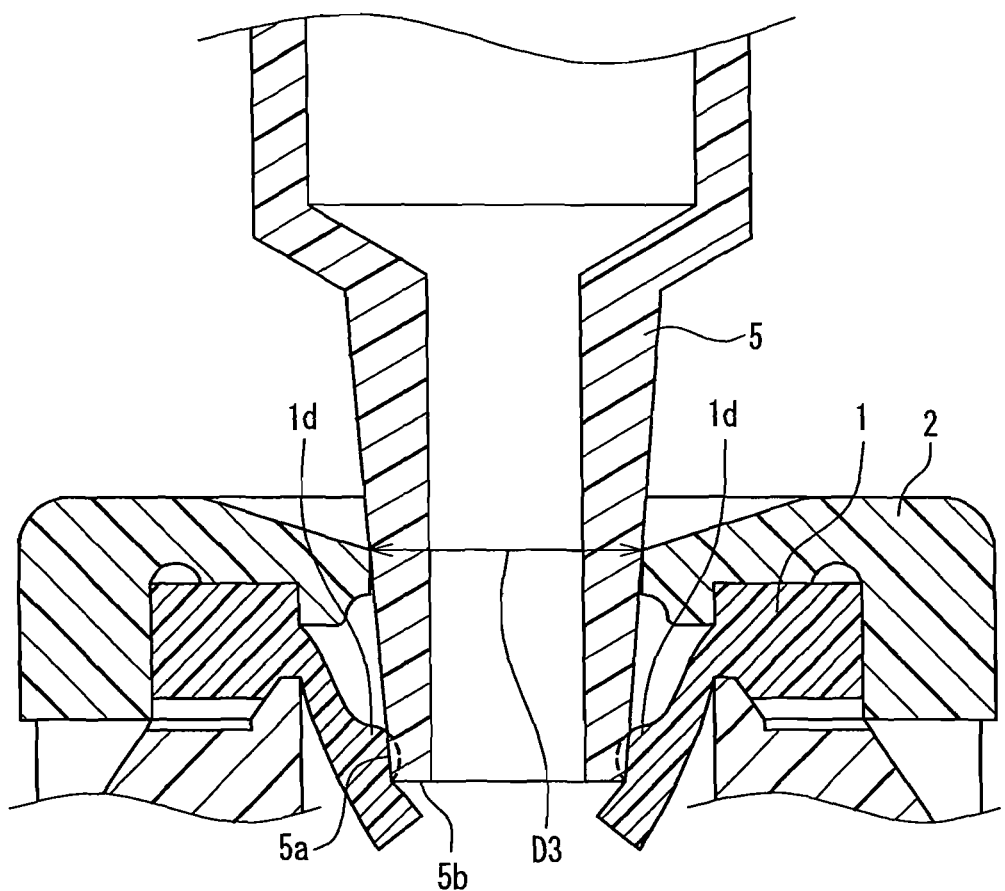
FIG. 10 is an explanatory diagram showing a situation in which an inserting body has been inserted into the medical port shown in FIG. 9 and the inserting body has been fitted into a fitting hole of the cover.

FIG. 9 shows a partial enlarged cross-sectional view of the example of the medical port of the present invention, and FIG. 10 shows a situation in which an inserting body 5 has been inserted into the example of the medical port of the present invention shown in FIG. 9 and the inserting body 5 has been fitted into the fitting hole 2a (see FIG. 1) of the cover 2. In FIG. 10, in order to facilitate understanding, the annular protrusion 1d that has been deformed under the pressure exerted by the inserting body is indicated by a solid line, and the annular protrusion 1d in an imaginary state in which the pressure by the inserting body is not exerted is indicated by a dotted line.

As shown in FIG. 10, the contact that is made between an outer circumferential surface 5a of the leading end portion of the inserting body 5 and the valve 1 more effectively contributes to the improvement of the sealing properties than the contact that is made between an end surface 5b of the leading end portion of the inserting body 5 and the valve 1. As shown in FIGS. 9 and 10, in the valve 1, a portion D of the stepped surface 11 (see FIG. 8) that is contiguous to the upper surface of the central portion 1a is unlikely to come in contact with the outer circumferential surface 5a of the leading end portion of the inserting body 5. Moreover, forming the annular protrusion 1d in the portion D increases the insertion resistance to the inserting body 5.

Therefore, in view of the compatibility between improvement of the sealing properties and good ease of insertion of the inserting body, it is preferable that the annular protrusion 1d is formed at a position in the above-described stepped surface 11 that is below the upper surface of the central portion 1a of the valve 1 so as to achieve a good contact between the outer circumferential surface 5a of the leading end portion of the inserting body 5 and the valve 1, which greatly contributes to the improvement of the sealing properties. More specifically, it is preferable that the valve central portion 1a has a diameter of 3.9 mm to 4.3 mm, the insertion hole 1f has a length of 2.8 mm to 3.9 mm in the longitudinal direction, and the fitting hole 2a has a diameter of 3.9 mm to 4.3 mm. In addition, in the case where the inserting body 5 is a luer defined in ISO 594-2, it is preferable that the annular protrusion 1d is formed at a position that is 0.2 mm to 0.6 mm below the upper surface of the central portion 1a of the valve 1 in the vertical direction. In this case, in view of the compatibility between improvement of the sealing properties and good ease of insertion of the inserting body, it is preferable that a relationship below is satisfied with respect to the annular protrusion 1d.

$$0.2 \leq (W2-W1)/2 \leq 0.6$$

Figure 11:
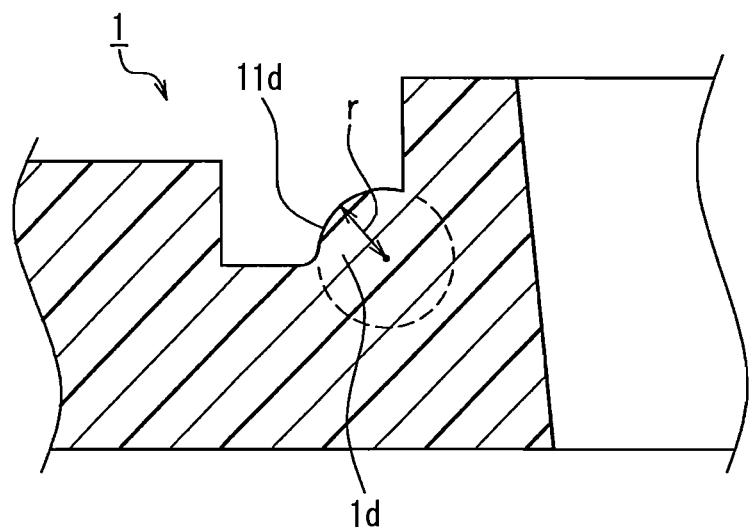
FIG. 11 is a partial enlarged cross-sectional view of the valve shown in FIG. 8.
Figure 12:
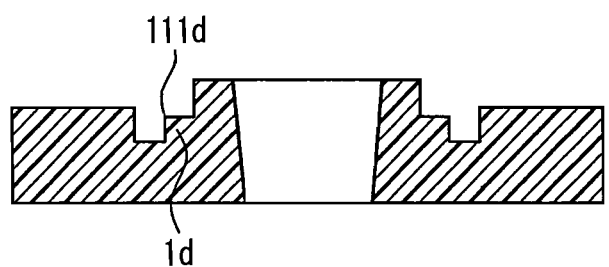
FIG. 12 is a cross-sectional view of a valve constituting another example of the medical port according to Embodiment 1 of the present invention.

W1: diameter (mm) of the central portion as seen when the valve 1 is viewed from above from its upper surface side W2: outer diameter (mm) of the annular protrusion as seen when the valve 1 is viewed from above from its upper surface side Moreover, as shown in FIG. 11, it is preferable that the annular protrusion 1d has a radiused surface 11d having a radius of curvature 1/r of more than 0 mm and not more than 0.4 mm. Alternatively, as shown in FIG. 12, the cross-sectional shape of the annular protrusion 1d may be an approximately triangular shape having an acute vertex angle 111d.

For example, as shown in FIG. 8, the thickness of the central portion 1a of the valve 1 may be set to a greater thickness than the thickness of the peripheral edge portion 1b. In this case, a step generated between the surface of the cover 2 and the upper surface of the central portion 1a of the valve 1 can be eliminated or reduced. Thus, even if a drug solution, blood, or the like adheres to the upper surface of the central portion 1a of the valve 1, such adhering matter preferably can be wiped off with ease.

The valve 1 has, for example, a circular or elliptical outer shape when viewed from above. Examples of the insertion hole 1f include a linear slit. If the inserting body is a luer defined in ISO 594-2, it is preferable that the insertion hole (slit) 1f in the upper surface of the valve 1 has a length $L0_U$ (see FIG. 7) of 2.8 mm to 3.9 mm in the longitudinal direction in view of the ease of insertion or the liquid tightness of the valve 1. Moreover, it is preferable that the ratio between the outer diameter D2 of the valve 1 and the slit length $L0_U$ is $1.1 \leq D2/L0_U \leq 4$. It is preferable that the peripheral edge portion of the valve 1 has a thickness L1 (see FIG. 8) of 1 mm to 2 mm in view of improvement of the ease of insertion of the inserting body into the valve 1, an effect of the valve 1 of allowing only one-way flow, economic efficiency, and the like. It should be noted the dimensions regarding the valve described in the present application are values determined in the state in which the valve 1 is not held by the cover 2 and the base seat 7.

Preferably, the slit length $L0_U$ is not less than 0.7 times and not more than 1.1 times the maximum outer diameter D3 (see FIG. 10) of a portion of the inserting body that is embedded in the valve 1 when the inserting body has been fitted into the fitting hole 2a.

A rubberlike elastic material can be used as the material constituting the valve 1. More specifically, however, a material having a JIS-A hardness of 20 to 55 is preferable, and a material having a JIS-A hardness of 30 to 40 is more preferable. Specific examples of the material include silicone rubber, natural rubber, synthetic rubber such as butyl rubber or nitrile rubber, thermoplastic rubber, or the like.

In the foregoing description, as an example of the medical port of the present invention, the coinjection port that can be provided in the midst of a liquid feed passage constituting an infusion set or the like is described by way of example using FIGS. 1 to 12. However, the applications in which the medical port of the present invention can be used are not limited to the coinjection port, and the medical port of the present invention can be applied to any medical device having a port for injection and/or collection of a drug solution, such as a mouth portion of a container containing or for containing a drug solution, a side injection tube of an infusion set, and the like.

Embodiment 2

Figure 13:
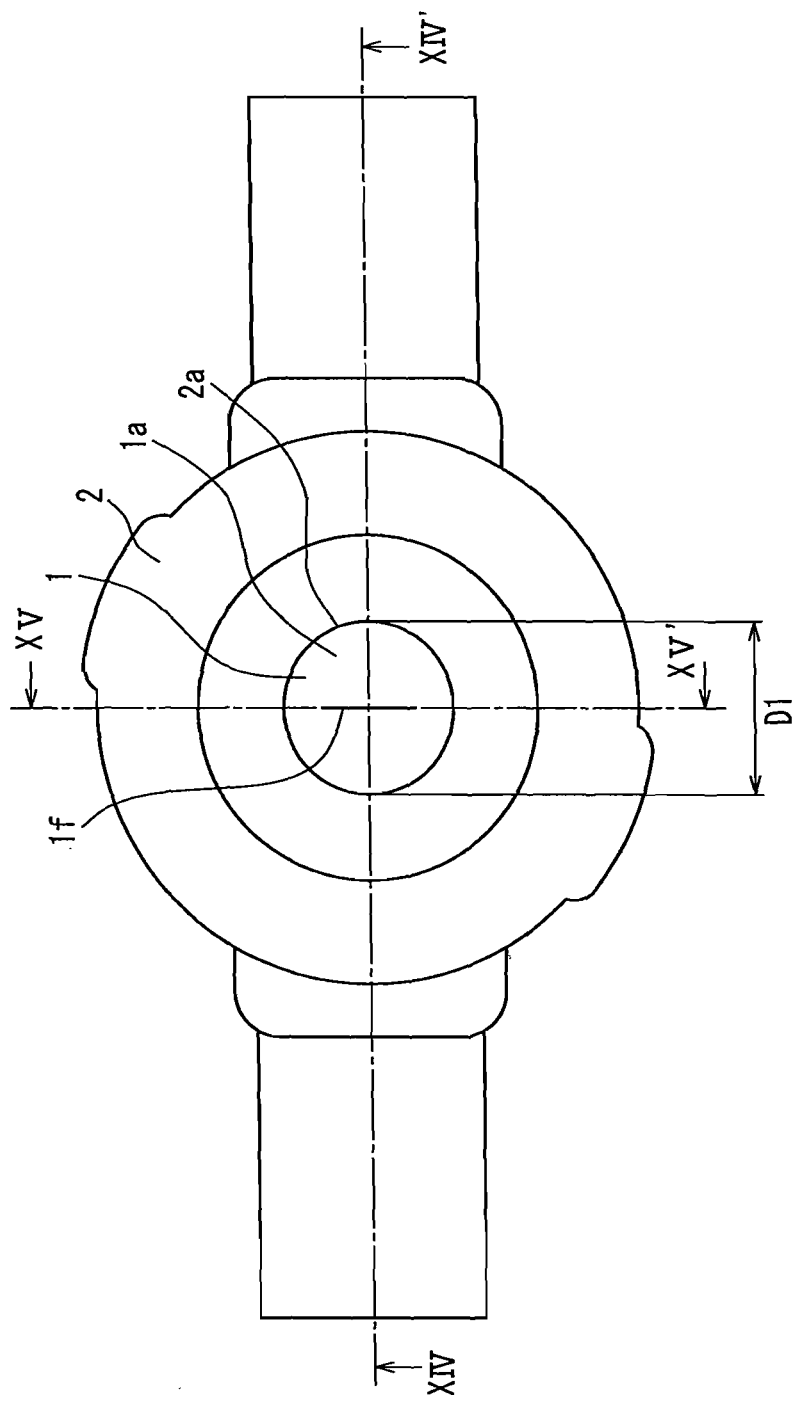
FIG. 13 is a plan view for explaining an example of a medical port according to Embodiment 2 of the present invention.
Figure 14:
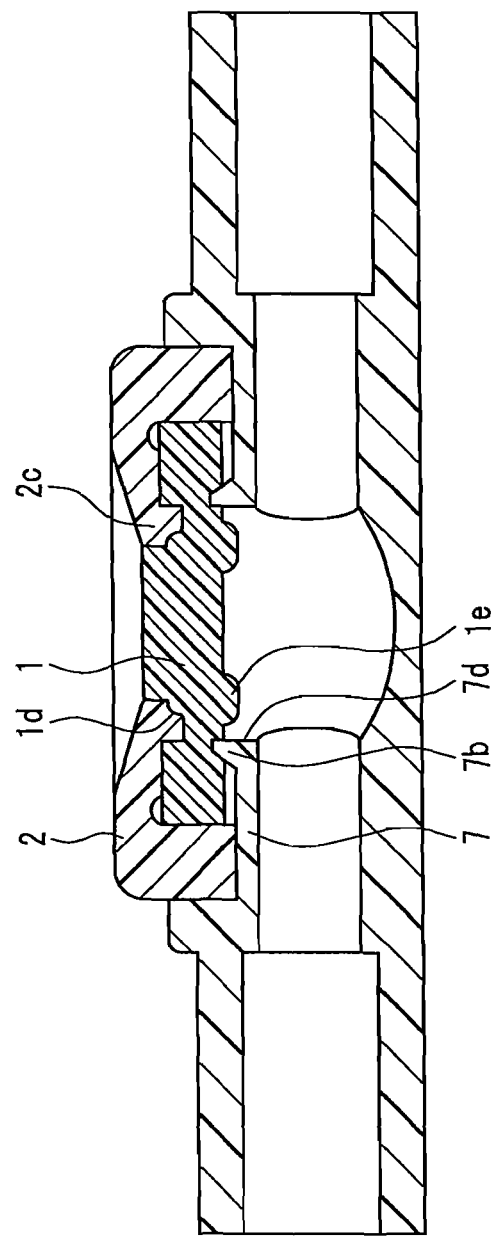
FIG. 14 is a cross-sectional view of the medical port shown in FIG. 13 taken along line XIV-XIV'.
Figure 15:
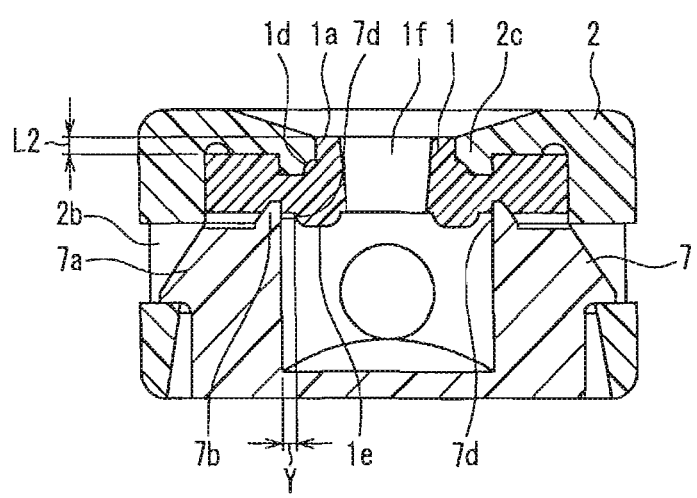
FIG. 15 is a cross-sectional view of the medical port shown in FIG. 13 taken along line XV-XV'.
Figure 16:
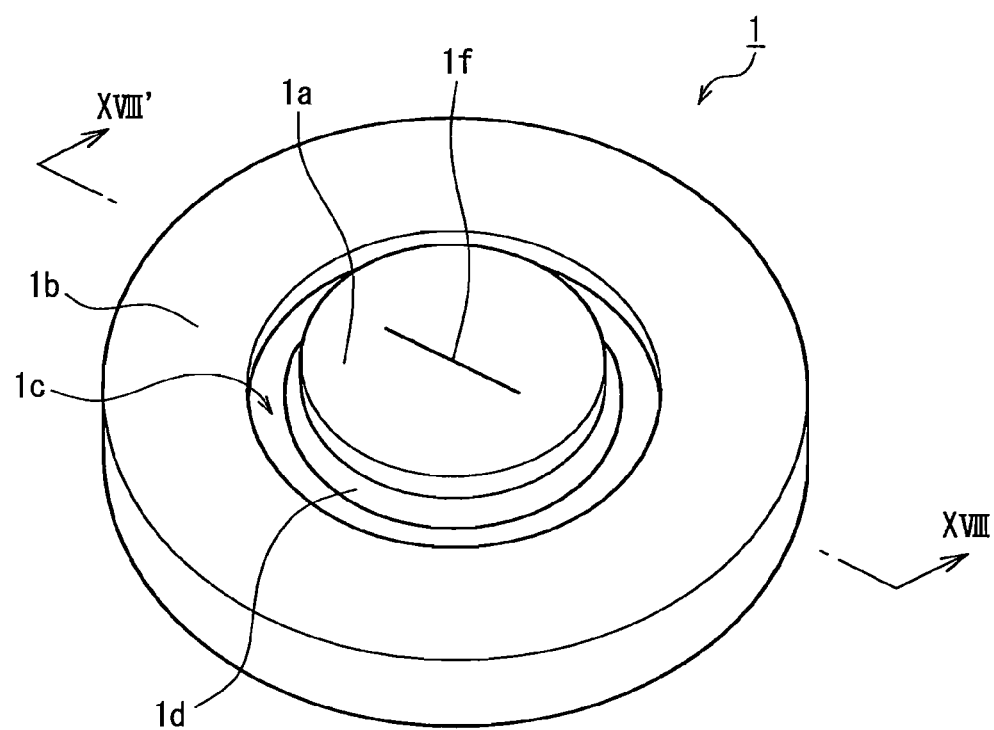
FIG. 16 is a perspective view of a valve constituting the medical port of the present invention shown in FIG. 13.
Figure 17:
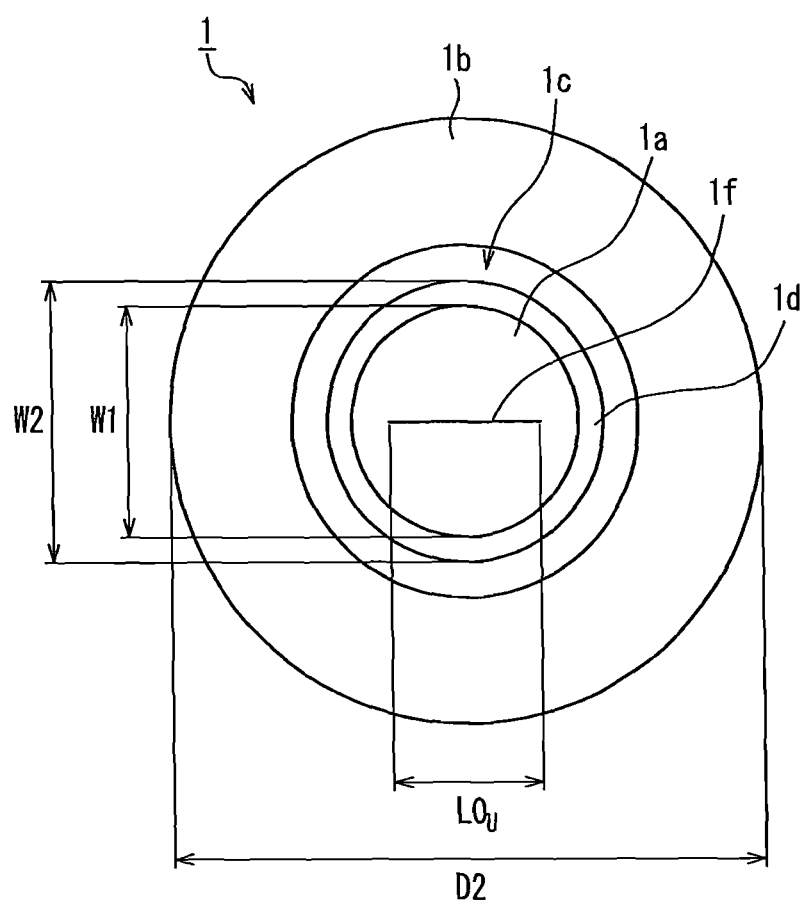
FIG. 17 is a plan view of the valve shown in FIG. 16.
Figure 18:
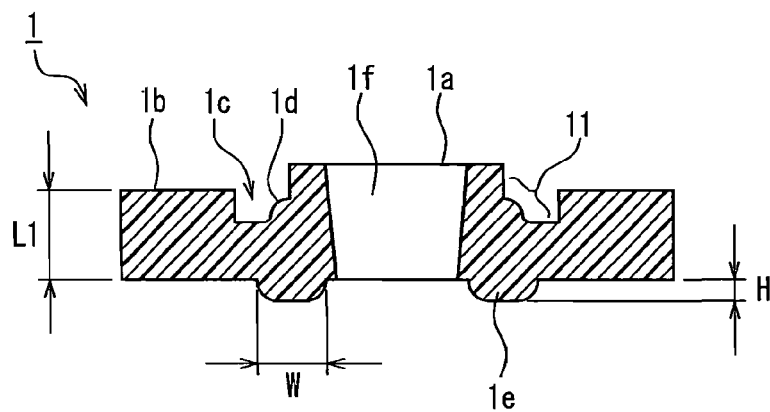
FIG. 18 is a cross-sectional view of the valve shown in FIG. 16 taken along line XVIII-XVIII'.

Next, an example of a medical port according to Embodiment 2 of the present invention will be described using FIGS. 13 to 21. FIG. 13 is a plan view of the example of the medical port according to the present embodiment, FIG. 14 is a cross-sectional view of the medical port of the present invention shown in FIG. 13 taken along line XIV-XIV', and FIG. 15 is a cross-sectional view of the medical port of the present invention shown in FIG. 13 taken along line XV-XV'.

In the lower surface of the valve 1 of the medical port of the present embodiment, protrusions are formed in respective positions that are on a straight line extending in the same direction as the longitudinal direction of the insertion hole 1f and in the vicinity of both ends of the insertion hole 1f in the longitudinal direction. Each protrusion, for example, defines part of a ring-shaped protrusion 1e that is formed so as to surround the insertion hole 1f. The medical port of the present embodiment otherwise has the same structure as the medical port of Embodiment 1. Thus, in FIGS. 13 to 21, like members are denoted by like reference numerals, and the descriptions of those members are omitted. Forming the above-described protrusions in the lower surface of the valve 1 as in the medical port of the present embodiment further improves the tightness of contact between the outer circumferential surface of the leading end portion of the inserting body and the valve 1 and further suppresses the occurrence of liquid leakage, and therefore is preferable.

Figure 19:
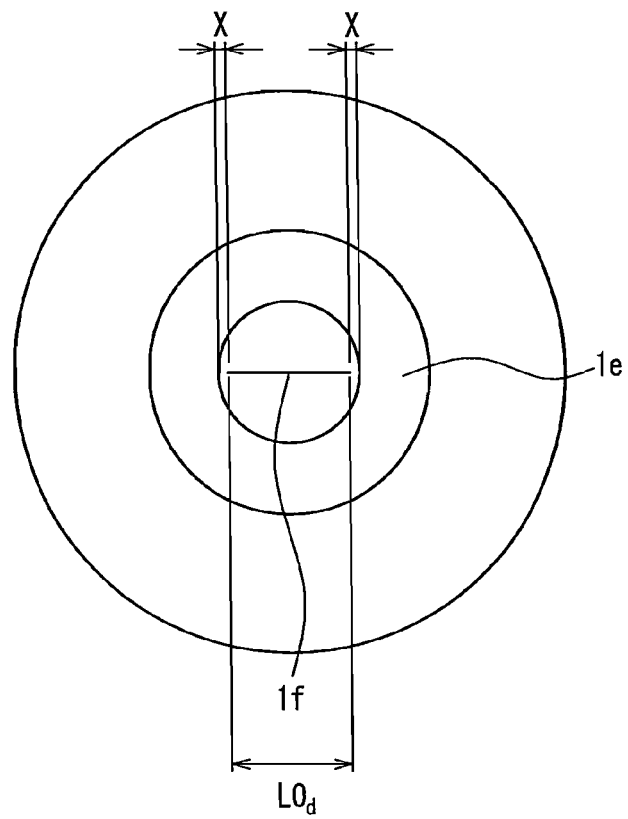
FIG. 19 is a bottom view of the valve shown in FIG. 16.
Figure 20:
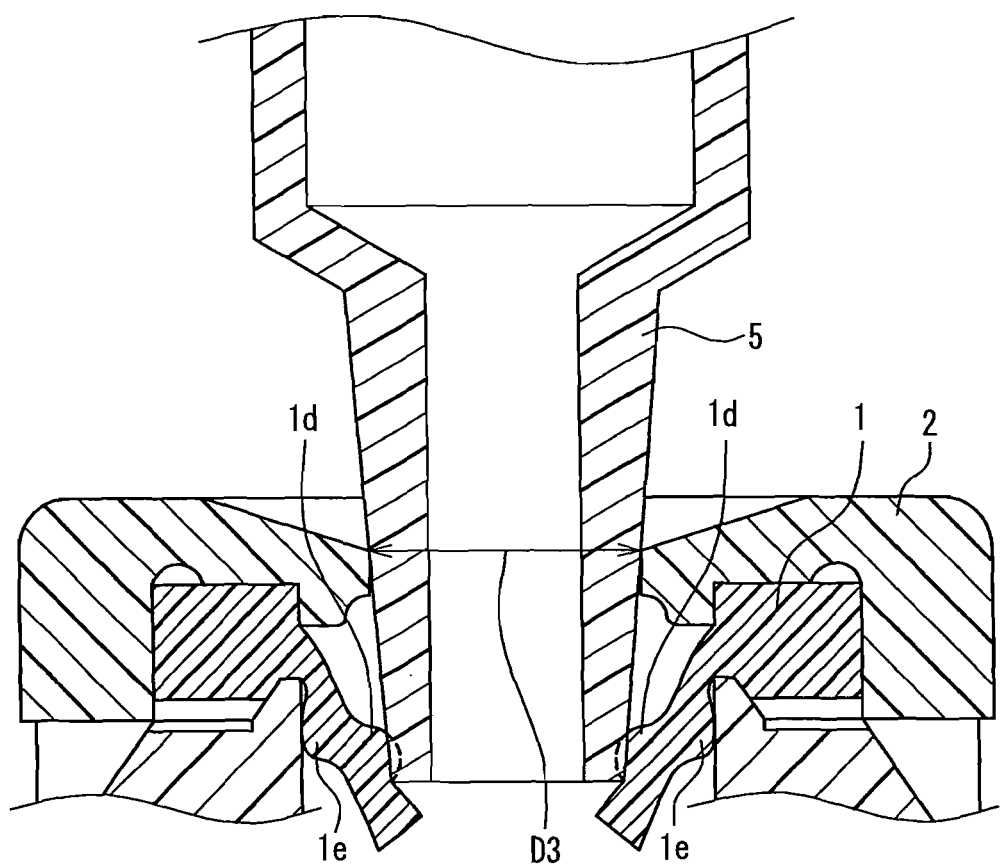
FIG. 20 is an explanatory diagram showing a situation in which an inserting body has been inserted into the medical port shown in FIG. 13 and the inserting body has been fitted into a fitting hole of a cover.

As shown in FIG. 19, the minimum distance X between the ring-shaped protrusion 1e and the insertion hole 1f on the lower surface of the valve 1, that is, the minimum distance X between portions of the ring-shaped protrusion 1e that are in the vicinity of both ends of the insertion hole 1f in the longitudinal direction and respective ends of the insertion hole 1f near those portions is preferably more than 0 mm and not more than 0.5 mm and more preferably more than 0 mm and not more than 0.15 mm in view of improving the tightness of contact and improving the effect of suppressing the occurrence of liquid leakage.

Although the minimum distance X between each of the portions (protrusions) of the ring-shaped protrusion 1e that are in the vicinity of both ends of the insertion hole 1f in the longitudinal direction and the insertion hole 1f is preferably more than 0 mm and not more than 0.5 mm, it is preferable that the minimum distance X is not less than 0.10 mm in light of reducing the possibility that, during formation of the insertion hole 1f using a cutter or the like, the ring-shaped protrusion 1e may be partly cut with the cutter, and consequently improving the productivity.

The maximum height H (see FIG. 18) of the ring-shaped protrusion 1e on the straight line (an extension of the insertion hole 1f) extending in the same direction as the longitudinal direction of the insertion hole 1f, that is, the maximum height H of each of the protrusions is preferably 0.2 mm to 0.5 mm and more preferably 0.15 mm to 0.30 mm in light of suppressing an increase in the insertion resistance during insertion of the inserting body into the insertion hole 1f while ensuring an enhanced effect of suppressing a crack in the valve.

There is no particular limitation to the maximum height of portions of the ring-shaped protrusion 1e other than the portions on the straight line (the extension of the insertion hole 1f) extending in the same direction as the longitudinal direction of the insertion hole 1f. However, it is preferable that the height of the ring-shaped protrusion 1e is constant along its circumferential direction because, for example, the valve easily can be shaped, and the limitation to the direction with respect to the longitudinal direction of the insertion hole can be removed during formation of the insertion hole. That is to say, it is preferable that the shape of a cutting plane of the ring-shaped protrusion 1e as seen when the protrusion is cut in a radial direction is the same whichever radial direction the ring-shaped protrusion is cut.

Although there is no particular limitation to the cross-sectional shape of the ring-shaped protrusion 1e, it is preferable that the height of portions near the ends of the insertion hole 1f is high in light of more effectively suppressing a crack in the valve. From the same point of view, it is preferable that not only the portions near the ends of the insertion hole 1f but also a portion away from those ends is high. Moreover, in light of suppressing tearing of part of the ring-shaped protrusion 1e due to friction or the like, the ring-shaped protrusion 1e preferably has such a shape that has no acute-angled portion. Accordingly, it is preferable that the ring-shaped protrusion 1e, for example, in the vicinity of both ends of the insertion hole 1f in the longitudinal direction, includes radiused surfaces such that the ring-shaped protrusion gradually increases in height from the side near the insertion hole 1f and the side away from the insertion hole 1f, and is flat at the top. Moreover, it is preferable that the ring-shaped protrusion 1e, at any position in the circumferential direction thereof, includes radiused surfaces such that the ring-shaped protrusion gradually increases in height from the inner circumferential side and the outer circumferential side, and is flat at the top.

Although there is no particular limitation to the width W (see FIG. 18) of the ring-shaped protrusion 1e, the ring-shaped protrusion is preferably 0.4 mm to 1.3 mm wide because at this width, the inserting body easily can be inserted into the insertion hole 1f. If the ring-shaped protrusion 1e has such a large width W that brings the ring-shaped protrusion 1e into contact with the base seat 7, the insertion resistance to the inserting body increases, so such a configuration is not preferable. Therefore, as shown in FIG. 15, it is preferable that the ring-shaped protrusion 1e and an opening wall surface 7d are apart in the state in which the inserting body is not inserted in the insertion hole 1f. Specifically, the distance between the ring-shaped protrusion 1e and the opening wall surface 7d, which forms a gap Y so that the ring-shaped protrusion 1e is not in contact with the annular projection 7b. The gap Y is preferably 0.1 mm or more, more preferably 0.2 mm or more, and even more preferably 0.4 mm or more.

The width W of the ring-shaped protrusion 1e may be constant along the circumferential direction or may vary. For example, the width of portions in the vicinity of both ends of the insertion hole 1f in the longitudinal direction may be larger than the width of other portions.

Figure 21:
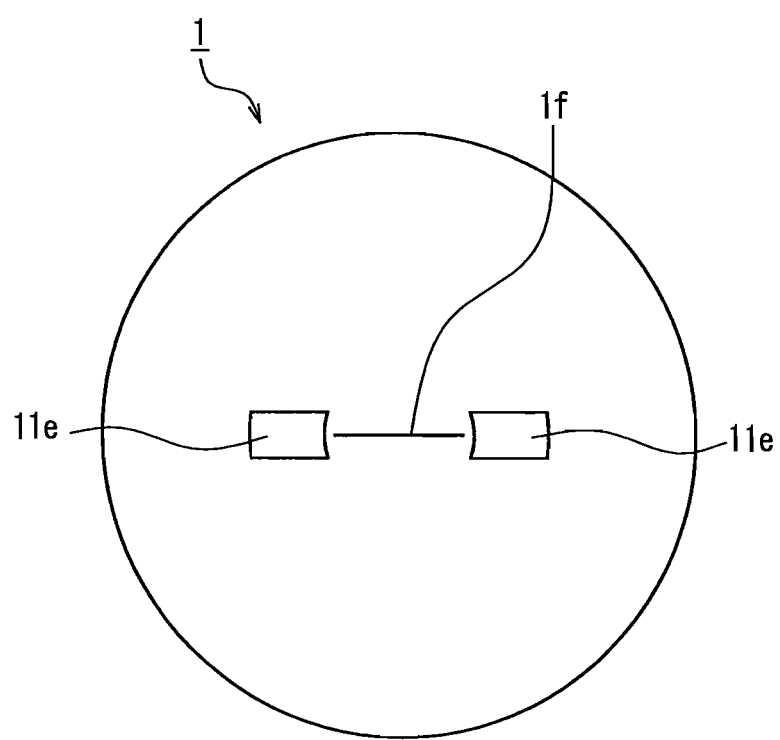
FIG. 21 is a bottom view of a valve constituting another example of the medical port according to Embodiment 2 of the present invention.

In still another example of the medical port of the present invention, as shown in FIG. 21, in the lower surface of the valve 1, protrusions 11e may be formed on the straight line extending in the same direction as the longitudinal direction of the insertion hole 1f and in the vicinity of both ends of the insertion hole 1f in the longitudinal direction. In this manner, a crack in the valve also can be suppressed in the case where the protrusions 11e having, for example, a maximum height of 0.2 mm to 0.5 mm are formed in predetermined positions (positions at which the minimum distance between the protrusions 11e and the insertion hole is, for example, more than 0 mm and shorter than 0.5 mm) that are located on the straight line (the extension of the insertion hole 1f) extending in the same direction as the longitudinal direction of the insertion hole 1f and at which a crack in the valve 1 seems likely to occur. If the respective protrusions 11e that are formed in the vicinity of both ends of the insertion hole 1f in the longitudinal direction define part of the ring-shaped protrusion 1e that is formed so as to surround the insertion hole 1f as shown in FIGS. 13 to 20, and the inner circumference of the ring-shaped protrusion as seen when the valve is viewed from above from its lower surface side has a circular shape, the limitation to the direction with respect to the longitudinal direction of the insertion hole 1f can be removed, so such a configuration is preferable. In this case, the limitation to the direction with respect to the longitudinal direction of the insertion hole 1f can be removed during formation of the insertion hole 1f by slitting the valve using a cutter or the like.

EXAMPLES

Medical ports of Examples 1 and 2 and Comparative Example 1 were made, and an airtightness test and an ease-of-insertion test were conducted on these medical ports as described below.

Example 1

Medical ports having the form shown in FIGS. 1 to 3 were made. In these medical ports, the diameter D2 (see FIG. 7) of the valve is 10 mm, the length $L0_U$ of the insertion hole (the slit) in the upper surface of the valve in the longitudinal direction is 3.1 mm, the length $L0_d$ of the insertion hole 1f in the lower surface of the valve 1 in the longitudinal direction is 2.9 mm, the diameter D1 (see FIG. 1) of the fitting hole is 4.2 mm, the outer diameter W1 (see FIG. 7) of the central portion as seen when the valve 1 is viewed from above from its upper surface side is 4.1 mm, the outer diameter W2 (see FIG. 7) of the annular protrusion as seen when the valve 1 is viewed from above from its upper surface side is 5.1 mm, the radius of curvature of the radiused surface of the annular protrusion is 0.1 mm, the thickness of the thinnest part of the annular groove 1c is 0.9 mm, the thickness L1 (see FIG. 8) of the portion 1b of the valve 1 outside the annular groove 1c is 1.5 mm, and the thickness of the central portion of the valve is 1.9 mm. The annular protrusion 1d is formed beginning at a position that is 0.4 mm below the upper surface of the central portion of the valve in the vertical direction. It should be noted that the longitudinal direction of the insertion hole (the slit) was set to the same direction as the longitudinal direction of the medical port. The material for the valve is an isoprene rubber, which has a hardness of 35 (JIS-A).

Example 2

Medical ports shown in FIGS. 13 to 15 were made. In these medical ports, the diameter D2 (see FIG. 17) of the valve 1 is 10 mm, the length LOU of the insertion hole (slit) 1f in the upper surface of the valve in the longitudinal direction is 3.1 mm, the length L0d of the insertion hole 1f in the lower surface of the valve 1 in the longitudinal direction is 2.9 mm, the diameter D1 (see FIG. 13) of the fitting hole 2a is 4.2 mm, the outer diameter W1 (see FIG. 16) of the central portion 1a as seen when the valve 1 is viewed from above from its upper surface side is 4.1 mm, the outer diameter W2 (see FIG. 7) of the annular protrusion as seen when the valve 1 is viewed from above from its upper surface side is 5.1 mm, the radius of curvature of the radiused surface of the annular protrusion is 0.1 mm, the distance X (see FIG. 19) between the ring-shaped protrusion 1e and each end of the insertion hole 1f is 0.15 mm, the maximum height H (see FIG. 18) of the ring-shaped protrusion 1e is 0.2 mm, the width W (see FIG. 18) of the ring-shaped protrusion 1e is 1.2 mm, the distance forming the gap Y (see FIG. 15) between the ring-shaped protrusion 1e and the opening wall surface 7d of the base seat 7 is 0.45 mm, the thickness of the thinnest part of the annular groove 1c is 0.9 mm, the thickness L1 (see FIG. 18) of the portion 1b of the valve 1 outside the annular groove 1c is 1.5 mm, and the thickness of the central portion of the valve is 1.9 mm. The annular protrusion 1d is formed beginning at a position that is 0.4 mm below the upper surface of the central portion of the valve in the vertical direction. It should be noted that the longitudinal direction of the insertion hole (the slit) was set to the same direction as the longitudinal direction of the medical port. The material for the valve is an isoprene rubber, which has a hardness of 35 (JIS-A).

Comparative Example 1

Medical ports having the same structure as those of Example 1 except that the annular protrusion is not formed were prepared as medical ports of Comparative Example 1.

Airtightness Test

Figure 22:
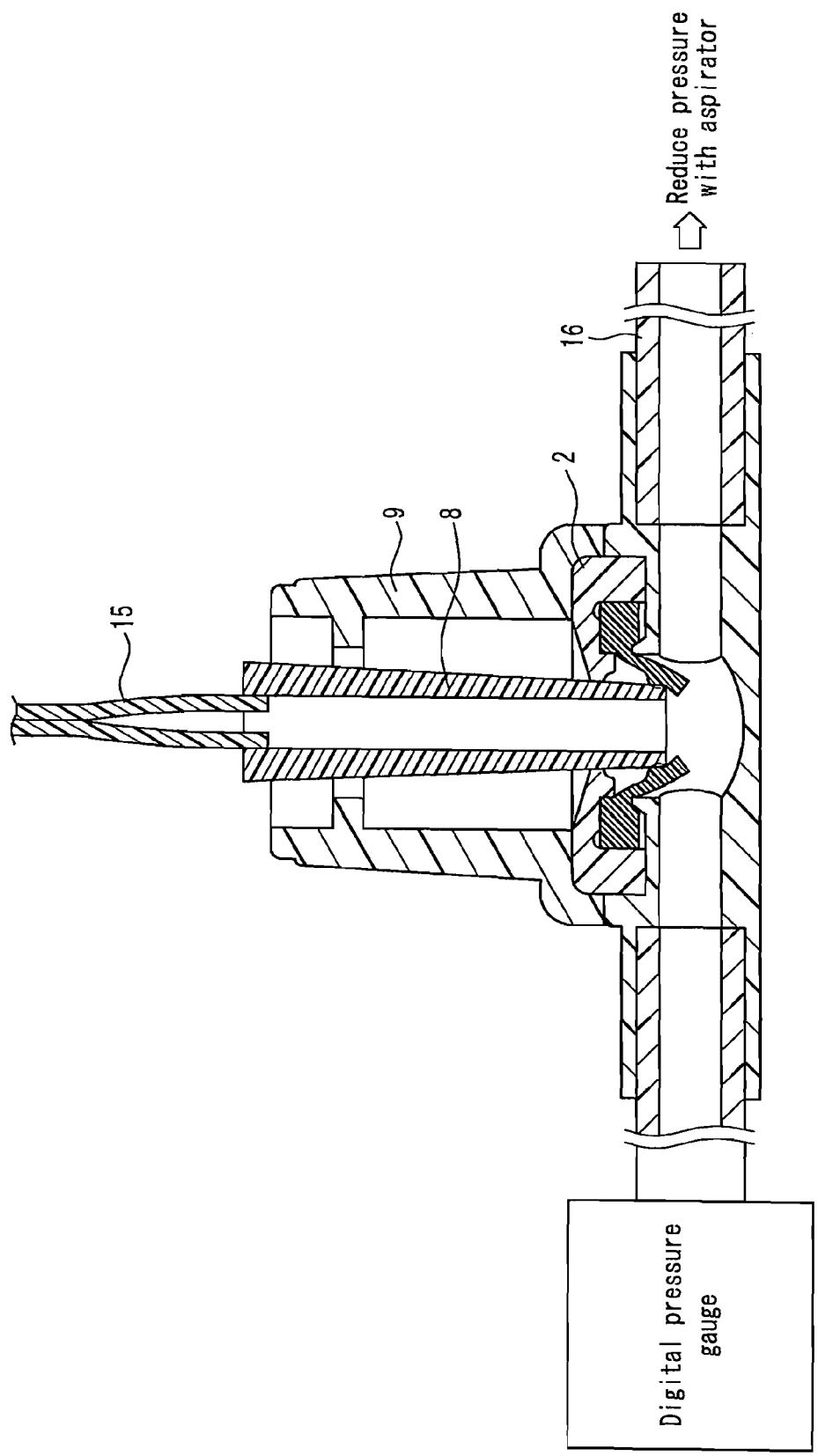
FIG. 22 is a conceptual diagram for explaining a manner in which an airtightness test was conducted.

Five each of the medical ports of Examples 1 and 2 and medical ports of Comparative Example 1 were left under an atmosphere at 70° C. for ten days. Then, with respect to each medical port, a luer 8 with a cover was inserted 200 times under a load of 10 N. Afterward, a system shown in FIG. 22 was assembled, and an airtightness test was conducted using the system. It should be noted that although the longitudinal direction of the insertion hole in FIG. 22 is perpendicular to the longitudinal direction of the medical port for ease of understanding of the airtightness test and for convenience of illustration, the longitudinal direction of the medical port actually is the same direction as the longitudinal direction of the insertion hole.

(1) A luer with a cover was fixed to a medical port by fitting the cover 9 of the luer to the cover 2 of the medical port. Then, a lumen of a tube 15 connected to one end of the luer with the cover was blocked. Subsequently, the pressure within the system shown in FIG. 22 was reduced to −70 kPa using an aspirator, and then a pressure reducing line 16 was closed to change the system shown in FIG. 22 to a closed system.

(2) Next, the luer 8 was inserted into the insertion hole of the medical port while being turned 360 degrees, and the luer 8 was fitted into the fitting hole of the cover 2 of the medical port.

(3) Next, the above-described luer 8 was inclined so that the central axis of the above-described luer 8 extended in the longitudinal direction of the insertion hole when viewing the medical port from above from the upper surface side of the valve, and the luer 8 was pushed further inward of the insertion hole.

(4) Next, the above-described luer 8 was inclined opposite to the direction of inclination in (3) so that the central axis of the above-described luer 8 extended in the longitudinal direction of the insertion hole when viewing the medical port from above from the luer 8 inserting side, and the luer 8 was pushed further inward of the insertion hole.

(5) If the value of the pressure within the system indicated by a digital pressure gauge increased by 0.1 kPa/sec or more during the operation in (2) to (4) above, it was determined that air contamination (leak) occurred, and the air contamination rate was calculated using a formula below.

Air contamination rate (%)=the number of samples with respect to which it was determined that air contamination occurred/the number of test samples ($n$=5)×100

The air contamination rate (%) of the medical ports of Example 1 was 60%, the air contamination rate (%) of the medical ports of Example 2 was 0%, and the air contamination rate (%) of the medical ports of Comparative Example 1 was 100%.

Insertion Force Measuring Test

Figure 23:
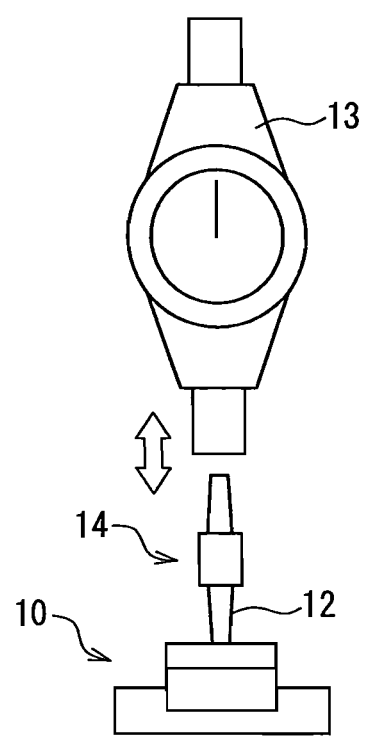
FIG. 23 is a conceptual diagram for explaining a manner in which an insertion force measuring test was conducted.

First, as shown in FIG. 23, a male connector (made of polycarbonate) 14 having a luer 12 defined in ISO 594-2 was disposed on the upper surface of the valve of a medical port 10 in such a manner that an end surface of the tip of the luer 12 was in contact with the upper surface of the valve. Then, after a load was applied to the male connector 14 for one second using a push-pull scale, the push-pull scale 13 was released from pressing against the male connector 14. The load at which an inserted state in which the male connector 14 was inserted in the insertion hole could be maintained for three seconds or more after the release of the push-pull scale 13 from pressing against the male connector 14 was measured as an insertion force. For each of the medical ports of Examples 1 and 2 and medical ports of the comparative example, the insertion force measurement was performed three times, and an average value of the insertion force regarding insertion of the inserting body into the insertion hole was obtained with respect to each medical port. It should be noted that the smaller insertion force means greater ease of insertion of the inserting body (smaller insertion resistance) and higher likelihood of the inserted state being maintained.

The average value of the insertion force regarding insertion of the inserting body into the insertion hole of the medical ports of Example 1 was 9.0 N, the average value of the insertion force regarding insertion of the inserting body into the insertion hole of the medical ports of Example 2 was 9.0 N, and the average value of the insertion force regarding insertion of the inserting body into the insertion hole of the medical ports of Comparative Example 1 was 11.7 N.

From the foregoing results, it was possible to confirm that the occurrence of liquid leakage is suppressed more with the medical ports of Examples 1 and 2 than with the medical ports of Comparative Example 1. In particular, in the case of the medical ports of Example 2, in which, in the lower surface of the valve, the protrusions are formed at the respective positions that are on the straight line (the extension of the insertion hole) extending in the same direction as the longitudinal direction of the insertion hole and in the vicinity of both ends of the insertion hole in the longitudinal direction, the air contamination rate (%) was extremely low, and thus it was possible to confirm that the occurrence of liquid leakage is suppressed even more in a more effective manner.

INDUSTRIAL APPLICABILITY

With the medical port of the present invention, the occurrence of liquid leakage is further suppressed. Thus, the medical port of the present invention is useful not only as a medical port constituting an infusion set but as a medical port constituting a transfusion set, a mouth portion of a container containing or for containing a drug solution, a side injection tube of an infusion set, and the like.

REFERENCE SIGNS LIST 1 valve
1a central portion
1b peripheral edge portion
1c annular groove
1d annular protrusion
1e ring-shaped protrusion
1f insertion hole
7 base seat
2 cover
2a fitting hole
2c annular hook portion
5 inserting body

The invention claimed is:

1. A medical port comprising:
a disc-shaped valve in which an insertion hole is formed in a central portion;
a base seat that supports the valve from a lower surface side and has a hole; and
a cover that has a fitting hole exposing an upper surface of the central portion of the valve and covers at least a peripheral edge of the valve from the upper surface side,
the fitting hole being formed so that when an inserting body has been inserted into the insertion hole and the hole of the base seat, a fit between the inserting body and the fitting hole can cause the inserting body to be locked against the cover,
wherein an annular protrusion is formed in the valve,
the annular protrusion being formed in a stepped surface that is formed by forming an annular groove around the central portion of the valve so that in a state in which the inserting body is locked against the cover, the annular protrusion is in contact with an outer circumferential surface of a leading end portion of the inserting body,
wherein the cover has an annular hook portion that can engage with the annular groove,
wherein the base seat has an annular projection that is formed along a peripheral edge portion of the hole provided in the base seat and that is positioned outwardly from the annular hook portion in a radial direction,
wherein a portion of the valve that is located outside the annular projection is compressed by the cover and the base seat,
wherein a ring-shaped protrusion located at a radially inner side of the annular projection and surrounding the insertion hole is formed on the lower surface of the valve so that portions of the ring-shaped protrusion are disposed on a straight line extending in the same direction as a longitudinal direction of the insertion hole and in the vicinity of both ends of the insertion hole in the longitudinal direction,
wherein the ring-shaped protrusion is spaced away from the insertion hole by a non-zero distance,
wherein the ring-shaped protrusion and an opening wall surface of the base seat are spaced apart by a distance forming a gap, so that the ring-shaped protrusion is not in contact with the annular projection, in a state in which the inserting body is not inserted in the insertion hole, wherein the open wall surface forms a wall surface of the hole, and
wherein the ring-shaped protrusion has a first radiused surface on a radially inner side of the ring-shaped protrusion, and a second radiused surface on a radially outer side of the ring-shaped protrusion, a height of the ring-shaped protrusion gradually increasing from the radially inner and outer sides toward a middle portion of the ring-shaped protrusion.

2. The medical port according to claim 1, wherein the annular protrusion is formed from a position in the stepped surface that is below the upper surface of the central portion of the valve.

3. The medical port according to claim 2, wherein the annular protrusion is formed from a position that is 0.2 mm to 0.6 mm below the upper surface of the central portion of the valve in a vertical direction.

4. The medical port according to claim 1, wherein the annular protrusion satisfies a relationship below:

$$0.2 \leq (W2-W1)/2 \leq 0.6$$

where $W1$ is an outer diameter (mm) of the central portion as seen when the valve is viewed from above from its upper surface side, and
$W2$ is an outer diameter (mm) of the annular protrusion as seen when the valve is viewed from above from its upper surface side.

5. The medical port according to claim 1, wherein the annular protrusion has a radiused surface having a radius of curvature of more than 0 mm and not more than 0.4 mm.

6. The medical port according to claim 1, wherein in the lower surface of the valve, a minimum distance between each of the portions of the ring-shaped protrusion disposed in the vicinity of both ends of the insertion hole in the longitudinal direction and the end of the insertion hole near that portion is more than 0 mm and not more than 0.15 mm.

7. The medical port according to claim 1, wherein a maximum height of each of the portions of the ring-shaped protrusion disposed in the vicinity of both ends of the insertion hole in the longitudinal direction is 0.2 mm to 0.5 mm.

8. The medical port according to claim 1, wherein an inner circumference of the ring-shaped protrusion as seen when the valve is viewed from above from its lower surface side has a circular shape.

9. The medical port according to claim 1, wherein the shape of a cutting plane as seen when the ring-shaped protrusion is cut in a radial direction is the same whichever radial direction the ring-shaped protrusion is cut.

10. The medical port according to claim 1, wherein the ring-shaped protrusion is located on a radially inner side of the opening wall surface of the base seat.

\* \* \* \* \*